(12) United States Patent
Olsen

(10) Patent No.: US 9,079,018 B2
(45) Date of Patent: Jul. 14, 2015

(54) IMPLANTABLE MEDICAL ELECTRICAL LEADS, KITS, SYSTEMS AND METHODS OF USE THEREOF

(75) Inventor: James M. Olsen, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 2690 days.

(21) Appl. No.: 11/566,639

(22) Filed: Dec. 4, 2006

(65) Prior Publication Data

US 2007/0168008 A1 Jul. 19, 2007

Related U.S. Application Data

(63) Continuation-in-part of application No. 11/256,220, filed on Oct. 21, 2005.

(60) Provisional application No. 60/742,122, filed on Dec. 2, 2005, provisional application No. 60/621,007, filed on Oct. 21, 2004.

(51) Int. Cl.
*A61N 1/05* (2006.01)

(52) U.S. Cl.
CPC ............ *A61N 1/0553* (2013.01); *A61N 1/0551* (2013.01)

(58) Field of Classification Search
CPC .................................................... A61N 1/0551
USPC ..................................................... 607/62, 116
See application file for complete search history.

(56) References Cited

U.S. PATENT DOCUMENTS

| | | | |
|---|---|---|---|
| 5,501,703 A | 3/1996 | Holsheimer | |
| 5,643,330 A | 7/1997 | Holsheimer | |
| 5,895,416 A * | 4/1999 | Barreras et al. | ................. 607/62 |
| 6,587,733 B1 | 7/2003 | Cross | |
| 7,212,867 B2 * | 5/2007 | Van Venrooij et al. | ....... 607/116 |
| 7,668,601 B2 | 2/2010 | Hegland | |
| 2004/0249429 A1 * | 12/2004 | Tadlock | ........................ 607/116 |
| 2005/0015130 A1 | 1/2005 | Gill | |
| 2006/0122678 A1 | 6/2006 | Olsen | |
| 2006/0173262 A1 | 8/2006 | Hegland | |

* cited by examiner

*Primary Examiner* — Catherine Voorhees
*Assistant Examiner* — Michael D Abreu

(57) ABSTRACT

Implantable medical electrical leads, kits, systems and methods of use thereof for electrically stimulating the spinal cord with a plurality of electric stimulation leads. Directional stimulation electrodes are disposed along the distal end portions of the leads to form an electrode array in the epidural space of a patient with at least first, second and third directional stimulation electrodes being oriented at determined angular orientations relative to the spinal cord or each other. The stimulation electrodes may be programmed to create a tripole in which at least the first, second and third directional stimulation electrodes are active.

12 Claims, 4 Drawing Sheets

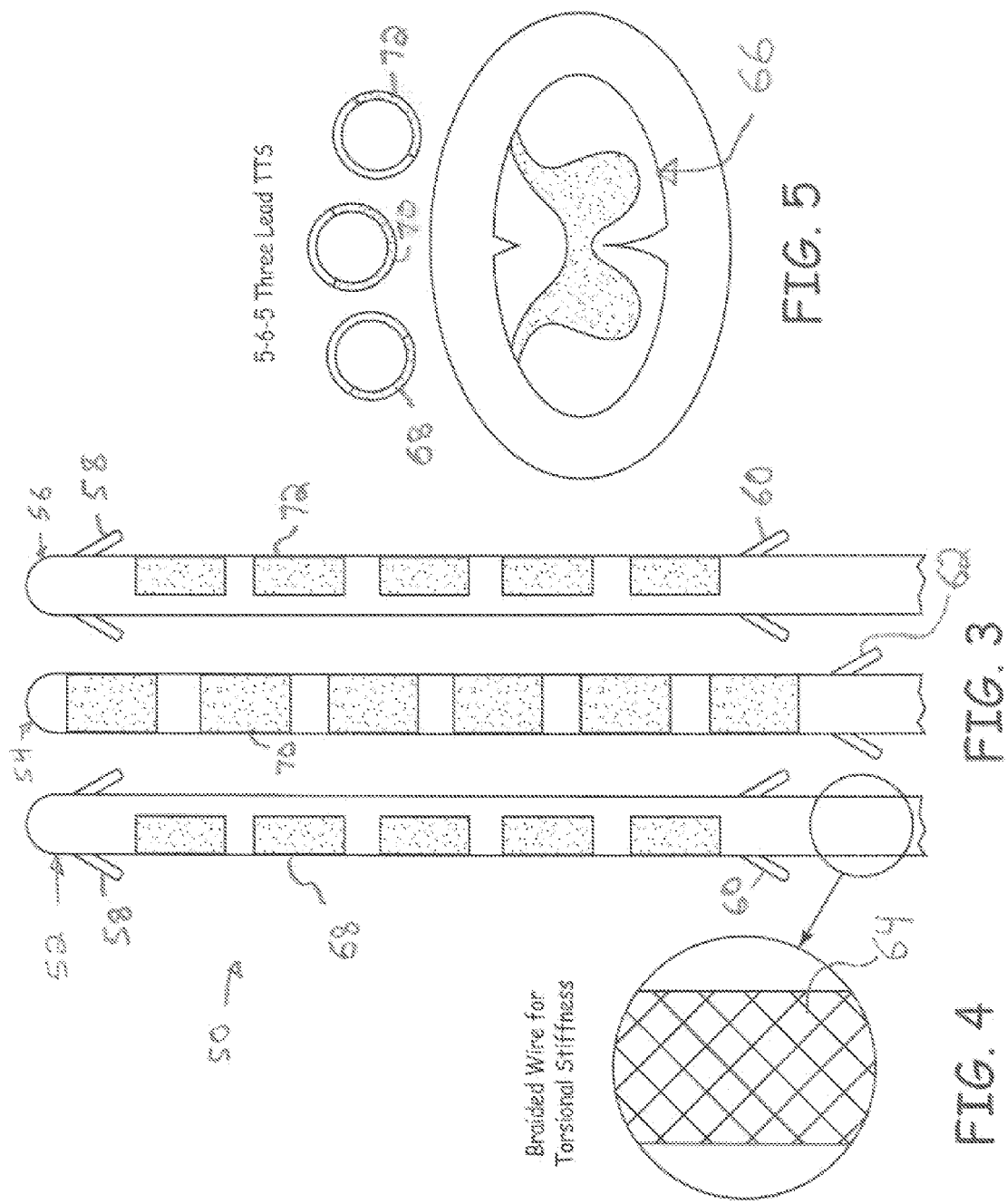

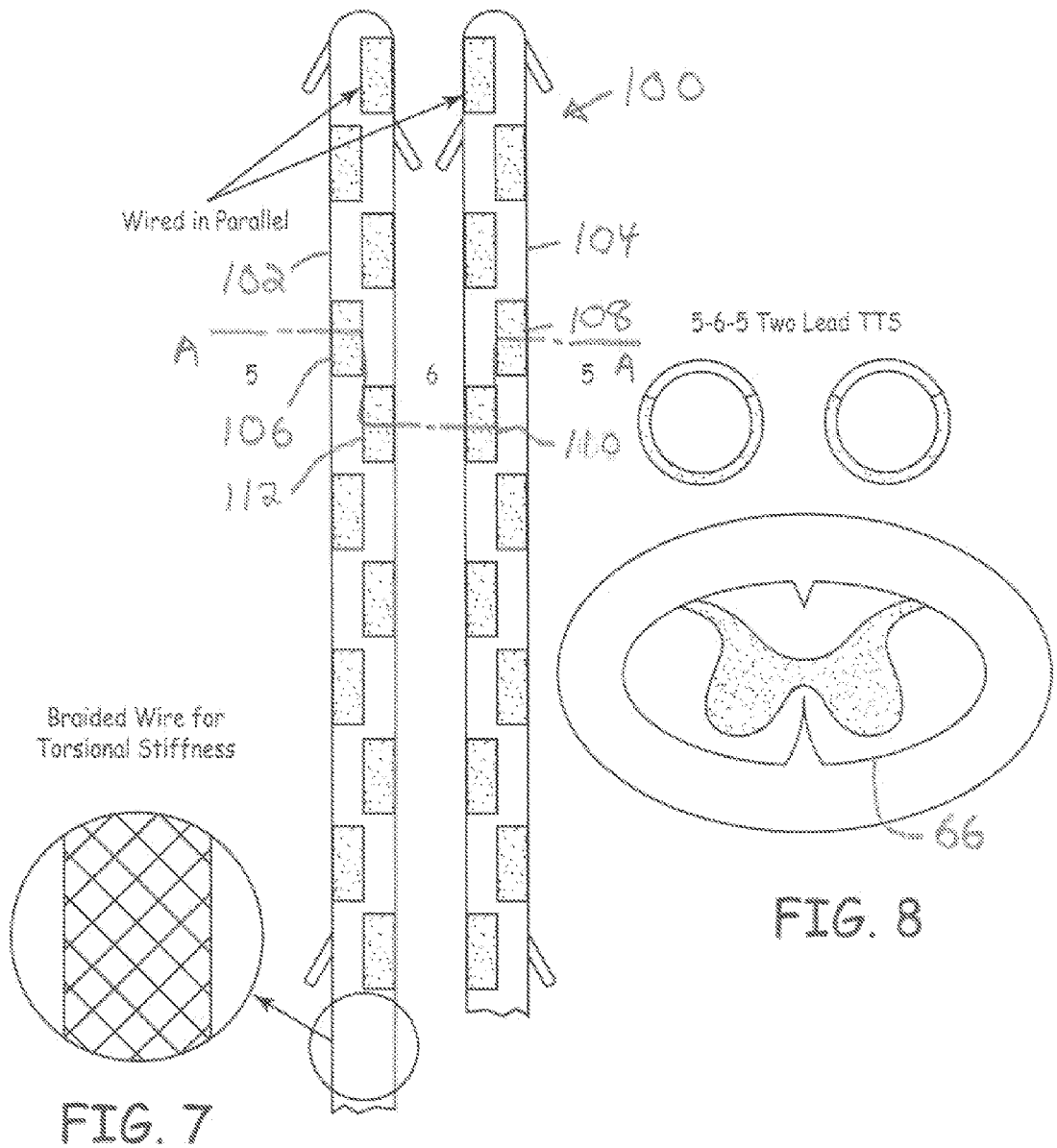

IMPLANTABLE MEDICAL ELECTRICAL LEADS, KITS, SYSTEMS AND METHODS OF USE THEREOF

RELATED APPLICATIONS

This application claims priority to provisional U.S. Application Ser. No. 60/742,122, filed Dec. 2, 2005. This application is also a continuation-in-part of, and claims priority to, U.S. patent application Ser. No. 11/256,220, filed Oct. 21, 2005, by James M. Olsen and Gary W. King, on Transverse Tripole Methods and Systems, which claims priority to U.S. provisional application No. 60/621,007, filed Oct. 21, 2004.

FIELD

This application relates to implantable medical electrical leads, kits including such leads, tissue stimulating systems and methods of use thereof, and more particularly to methods and systems for neurostimulation, for example, of the spinal cord with a tripole orientated generally transverse to the axis of the spinal cord.

BACKGROUND

Transverse tripole stimulation ("TTS") may involve, for example, at least three electrodes arranged substantially along a line approximately perpendicular or otherwise transverse to the axis of the spinal cord. The electrical field can be steered from side to side by varying the current or voltage between the center electrode and the outer electrodes. Voltages or currents can be in phase (overlapping in time) or out of phase between the right and left side. Using the outer electrodes as anodes may prevent nerve root stimulation.

See, e.g., U.S. Pat. Nos. 5,501,703; 5,643,330 and 5,895,416.

BRIEF SUMMARY OF EXEMPLARY EMBODIMENTS

As used herein, the term, "exemplary" is used in the sense of "for example" or "for purposes of illustration," and not in a limiting sense. The term "preferably" is used in the sense of a preference, as an option, and not in a limiting or mandatory sense.

Exemplary embodiments provide a lead kit or method in which directional electrodes (electrodes that extend less than the 360 degrees of conventional ring electrodes) may be employed on generally cylindrical leads to form a directional electrode array for complex stimulation patterns, such as tripoles (e.g., transverse tripoles), and which electrode arrays provide relatively energy efficient electrical stimulation of targeted tissue, such as spinal cord stimulation, while reducing the likelihood to stimulating non-targeted tissue, such as nerve roots.

An exemplary method generally comprises percutaneously implanting the first, second and third leads generally as illustrated in FIGS. 3-5 in the epidural space of a patient, and programming directional stimulation electrodes to create a tripole in which at least one electrode is active on each of the first, second and third lead. Preferably, voltage or current of each of the stimulation electrodes programmed in the programming step are independently controlled.

A second exemplary method comprises percutaneously implanting the first and second leads generally as illustrated in FIGS. 6-8 in the epidural space of a patient, with the leads being configured to provide three or four columns of segmented or directional electrodes, and programming the stimulation electrodes to create a tripole in which at least one electrode is active on each of at least three columns.

A third exemplary method of electrically stimulating the spinal cord involves use of a plurality of electric stimulation leads. Each of the electric stimulation leads has a distal end portion with a generally cylindrical cross section on which one or more directional stimulation electrode(s) are disposed. The directional stimulation electrodes form an electrode array including at least first, second and third directional stimulation electrodes with at least one of the first, second and third directional stimulation electrodes on a different electric stimulation lead than the other of the first, second and third directional stimulation electrodes. The method of this example generally comprises (a) implanting the plurality of electric stimulation leads in the epidural space of a patient with (1) the plurality of electric stimulation leads forming a lead array in the epidural space, and (2) the first, second and third directional stimulation electrodes being oriented at determined angular orientations relative to the spinal cord; and (b) programming the stimulation electrodes to create a tripole in which the first, second and third directional stimulation electrodes are active.

A fourth exemplary method of electrically stimulating the spinal cord involves use of first, second and third electric stimulation leads. Each of the first, second and third electric stimulation leads has a distal end portion with a generally cylindrical cross section and at least one stimulation electrode having an exposed, tissue-stimulating portion extending over less than half of the circumference of the distal end portion. The method of this example generally comprises (a) implanting the first, second and third electric stimulation leads in the epidural space of a patient with (1) the first, second and third electric stimulation leads forming a lead array in the epidural space in which the third electric stimulation lead is disposed between the first and second electric stimulation leads, and (2) the exposed, tissue-stimulating portions of the electrodes of each electric stimulation lead being oriented at determined angular orientations relative to the spinal cord; and (b) programming the stimulation electrodes to create a tripole in which at least one electrode is active on each of the first, second and third electric stimulation leads.

A fifth exemplary method of electrically stimulating the spinal cord involves use of first and second electric stimulation leads. Each of the first and second electric stimulation leads having a distal end portion with a generally cylindrical cross section. The first electric stimulation lead has a first stimulation electrode on the distal end portion thereof with an exposed, tissue-stimulating portion extending over less than half the circumference of the distal end portion. The second electric stimulation lead has second and third stimulation electrodes on the distal end portion thereof with each of the second and third stimulation electrodes having an exposed, tissue-stimulating portion extending over less than half of the circumference of the distal end portion. The method of this example generally comprises (a) implanting the first and second electric stimulation leads in the epidural space of a patient with (1) the first and second electric stimulation leads forming a lead array in the epidural space, and (2) the exposed, tissue-stimulating portions of the first, second and third stimulation electrodes being oriented at determined angular orientations relative to the spinal cord; and (b) programming the stimulation electrodes to create a tripole in which the first, second and third stimulation electrodes are active.

A sixth exemplary method of electrically stimulating the spinal cord involves use of first, second and third electric stimulation leads. Each of the first, second and third electric stimulation leads has a distal end portion with a generally cylindrical cross section on which one or more stimulation electrode(s) are disposed including first and second directional stimulation electrodes on the first and second electric stimulation leads, respectively, and a third stimulation electrode on the third stimulation lead. In this example, the third stimulation electrode may be either a conventional ring electrode or a directional electrode. The method of this example generally comprises (a) implanting the plurality of electric stimulation leads in the epidural space of a patient with (1) the plurality of electric stimulation leads forming a lead array in the epidural space with the third stimulation lead disposed between the first and second stimulation lead, and (2) the first and second directional stimulation electrodes being oriented at determined angular orientations relative to the spinal cord; and (b) programming the stimulation electrodes to create a tripole in which the first, second and third stimulation electrodes are active.

Additional exemplary embodiments include kits comprising two or three leads configured with directional or segmented electrodes, and to systems including such leads and an implantable pulse or signal generator.

BRIEF DESCRIPTION OF THE DRAWINGS

FIGS. 3-5 illustrates a three lead arrangement that may be used to provide transverse tripole stimulation.

FIGS. 6-8 illustrates a two lead arrangement that may also be used to provide transverse tripole stimulation.

DETAILED DESCRIPTION OF EXEMPLARY EMBODIMENTS

When used in the context of a lead, the term "longitudinal" refers to the direction of elongation of the lead, or to the substantially common direction of elongation of a plurality of substantially parallel leads (including without limitation leads placed alongside one another in the epidural space). "Lateral," when used in the context of a lead, refers to the direction generally perpendicular to the longitudinal direction of the lead or substantially parallel leads. When used in the context of the spinal cord, "longitudinal," "lateral" and "medial" are used in their common medically accepted meanings, e.g., "longitudinal" refers to the axial direction of the spinal cord. The term "transverse" when used in the context of a lead or electrode array relative to the spinal cord includes both the lateral direction relative to the spinal cord and diagonal directions relative to the spinal cord but in either case the term "transverse" implies some crossing over a center line or point defined with respect to the spinal cord or a central lead. All such terms are intended to have approximate practical meanings in view of the limp structure of exemplary preferred leads and the environment of use, rather than precise geometrical meanings.

In the context of a lead, "distal" means the longitudinal direction along the lead toward the free end of the lead (e. g., typically the end with tissue stimulating electrodes), and "proximal" refers to the longitudinal direction toward the end of the lead that is intended to be connected to an implantable neurostimulator 22, or a lead extension that is intended to connect the lead with such an neurostimulator 22. Because some exemplary leads may be typically somewhat flexible and limp such that the distal and proximal ends of the leads in a mechanical sense could be brought together, it will be understood that proximal and distal refer to relative positions along the length of the lead rather than a coordinate grid in absolute space.

Figure 1:
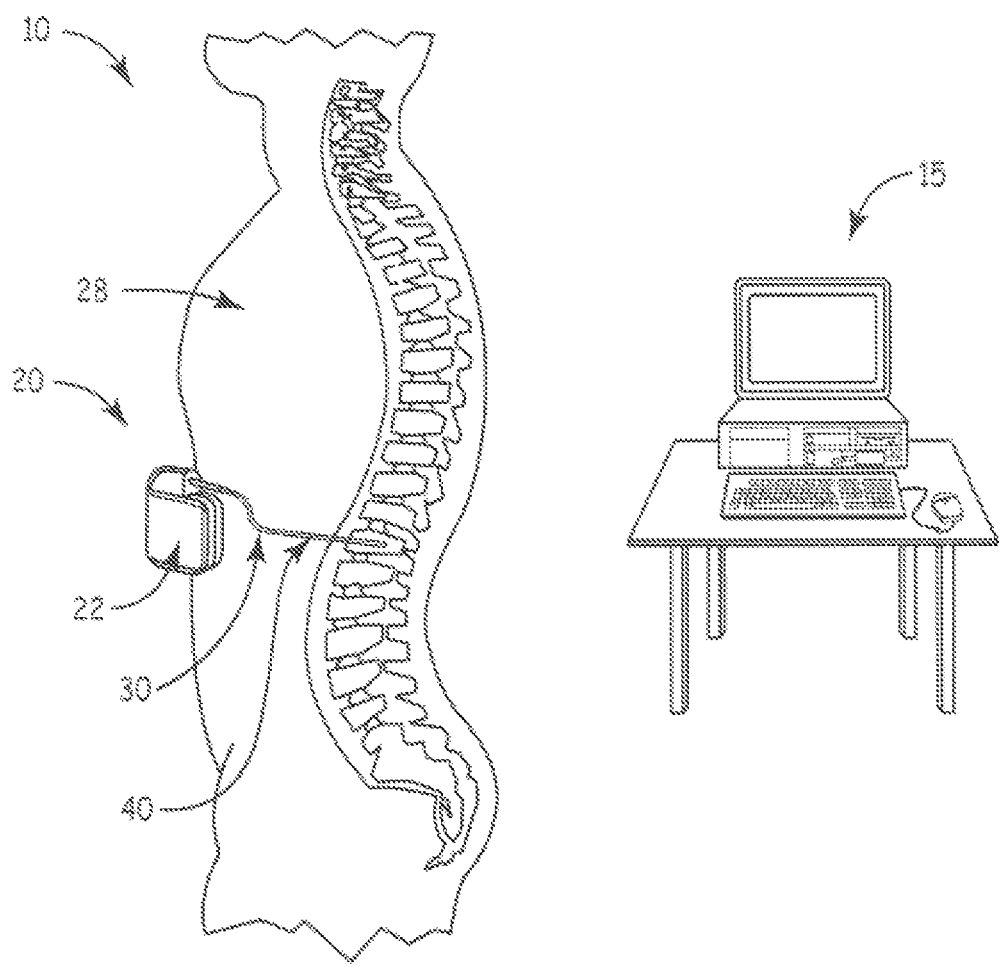
FIG. 1 shows a general environmental view for an embodiment of a neurostimulation system used to stimulate the spinal cord.
Figure 2:
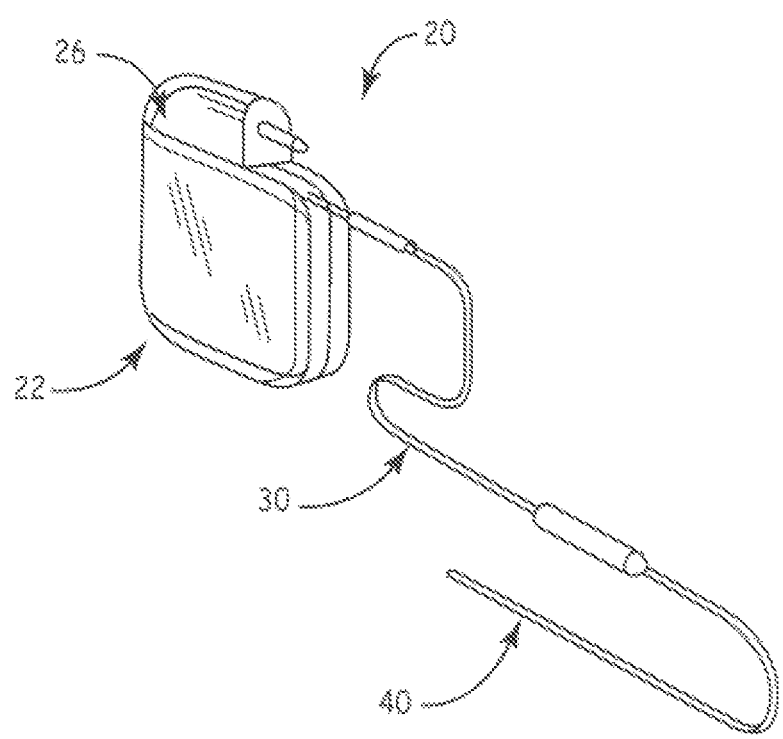
FIG. 2 shows the neurostimulation system of FIG. 1.

FIG. 1 shows a general environmental view 10 for an exemplary implantable neurostimulation system embodiment. Neurostimulation systems may be used to treat conditions such as pain, movement disorders, pelvic floor disorders, gastroparesis, and a wide variety of other medical conditions. As illustrated in FIGS. 1 and 2, the neurostimulation system 20 may include a neurostimulator 22, one or more stimulation lead extension(s) 30, and one or more stimulation lead(s) 40 (preferably three leads as illustrated in FIGS. 4-16). The neurostimulator 22 is typically implanted subcutaneously in the patient's body 28 at a location selected by the clinician. The stimulation lead 40 is typically fixed in place near the location selected by the clinician using a device such as an adjustable anchor.

The exemplary implantable neurostimulator 22 has a housing, a power supply in the housing 24, and stimulation electronics in the housing in electrical communication with the battery and in electrical communication with a connector block 26, which is also known as a terminal block.

The implantable neurostimulator 22 may be configured to provide current controlled pulses, voltage controlled pulses or both. The pulses are preferably independently variable (e.g., programmable) so that the voltage or current of each active electrode can be independently controlled. In current controlled embodiments, it is contemplated that each electrode could be an independently controllable current source or independently controllable current sink. An alternative embodiment of a current controlled-type neurostimulator 22 may include one or more electrodes that are programmed to be a voltage reference with other electrodes programmed to be current sources or current sinks. It is contemplated that such independent control may be obtained by any suitable manner, including, for example, by use of a switched matrix or by hardwiring independently controlled regulators, one for each electrode.

The exemplary stimulation lead 40 has a proximal end portion 45, a distal end portion 41 and a lead body 43 extending between the proximal end portion 45 and distal end portion 41. The proximal end portion 45 has electrical connectors 46 (also known as electrical terminals or contacts) for electrical connection with an IPG or lead extension. The distal end portion 41 has electrodes 42 discussed below. There is at least one lead conductor contained in the lead body that is electrically connecting the electrical connector 46 to the stimulation electrode 42. Typically, at least one conductor may be used to establish electrical communication between a single electrical connector/electrode pair, although alternative examples include multiplexing or bus features within the lead to allow use of fewer conductors along the length of the lead than the number of electrodes. As used herein, "conductive means" or "means for electrical communication between electrodes and electrical connectors" include the foregoing examples or any alternative structure that allows selection or electrical activation of one or more electrode.

At least one exemplary embodiment of the preferred stimulation leads includes such leads as are designed for percutaneous implantation, for example, through one or more needles rather than by a more invasive cut-down procedure. As used in this context, a "percutaneous" lead may be fully implanted, that is, it does not imply that some portion of the lead extends through the skin following implantation. Such percutaneous leads typically have a generally cylindrical configuration with ring electrodes 42 in the distal end portion and ring contacts 46 in the proximal end portion. In the preferred exemplary embodiment, the leads include directional, segmented or partial ring electrodes, each of which extends along an arc less than 360 degrees (e.g., 90-120 degrees) along the circumference of the lead.

The leads containing directional or segmented electrodes illustrated in FIGS. 3-5 and 6-8 may be used, for example, to improve field steering, prevent dorsal side stimulation, and improve battery life of the implantable pulse or signal generator (e.g., neurostimulator), sometimes referred to as an IPG.

In one exemplary embodiment, the segmented or directional electrode structure may be formed, for example, as follows: Each electrode ring may be a separate metal cylinder with a non active part covered with polymer insulation, and an active part (or region) exposed (i.e., not covered by the polymer insulation) such that the active part is adapted to provide electrical stimulation to tissue and the shielded part is shielded so that electrical stimulation is not provided by the non active part. The non active part may be slightly recessed to provide room for the insulation. U.S. patent application Ser. No. 10/008,773, filed Dec. 5, 2001, published as U.S. Patent Publication No. 2002/0183817, by Van Venrooij, assigned to Medtronic, Inc., on directional brain stimulation and recording leads, and U.S. Pat. No. 6,587,733, by Cross et al, assigned to Medtronic, Inc., are incorporated herein by reference. In these examples, each of the first, second and third active electrodes 68, 72 and 70 of FIGS. 3-5, or each of the first, second, third and fourth active electrodes 106, 108, 110 and 112 of FIGS. 6-8, may constitute conventional ring electrodes, which are shielded to provide electrical insulation over a portion of the electrode with an exposed, tissue-stimulating portion of the electrode being exposed through a window that remains unshielded.

Other exemplary segmented or directional electrodes in a cylindrical lead and methods of manufacturing such electrode structures are described in (a) U.S. patent application Ser. No. 10/469,423, filed Aug. 20, 2004, published as U.S. Patent Publication No. 2005/0015130, by Steven Gill, assigned to Medtronic, Inc., on "Brain Electrode"; (b) U.S. patent application Ser. No. 11/343,752, filed Jan. 31, 2006, published as U.S. Patent Publication No. 2006/0168805, by Michael Hegland and Richard Stone, assigned to Medtronic, Inc., on "Method Of Manufacturing A Medical Lead"; and (c) U.S. patent application Ser. No. 11/343,667, filed Jan. 31, 2006, published as U.S. Patent Publication No. 2006/0173262, by Michael Hegland and Richard Stone, assigned to Medtronic, Inc., on "Medical Lead With Segmented Electrode"; each of which is also incorporated herein by reference. In these examples, the first, second and third active electrodes 68, 72 and 70 of FIGS. 3-5, or each of the first, second, third and fourth active electrodes 106, 108, 110 and 112 of FIGS. 6-8, may each constitute an arcuate member extending less than half of the circumference of the distal end portion of the first, second or third electric stimulation lead 52, 56 or 54, respectively.

The active part may extend only around a portion of the circumference of the lead, such as about 180 degrees or less, for example 30-45 degrees. In at least one exemplary embodiment, however, each electrode may have an active region that covers approximately 90 to 270 degrees. FIG. 5 illustrates an exemplary embodiment in which the first and second directional stimulation electrodes (right and left side electrodes) each have an exposed, tissue-stimulating portion extending less than half of the circumference of the distal ends of the first and second electric stimulation leads respectively, and the third directional stimulation electrode (center electrode) has an exposed, tissue-stimulating portion extending more than half of the circumference of the distal end of the third electric stimulation lead.

Maintaining the angular orientation of the electrodes relative to the anatomy (tissue targeted for electrical stimulation) may be accomplished, for example, by any one or more of the following: 1) torsional stiffness provides by braided wire (e.g., braided wire 64 in FIG. 4) imbedded in the jacket and with an anchor on the fascia (e.g., a the type of anchor conventionally used to anchor percutaneous leads), 2) tines on the lead near the electrodes (e.g., tines 58, 60 or 62), 3) sigma shaped portions of the lead (proximal and/or distal to the electrodes).

If tines or sigma shaped features are used, they may help prevent contact between close proximity electrodes, otherwise special features may be employed to accomplish this, such as recessed electrodes or small raised rings on the leads near the electrodes.

Special extensions may be used to connect the three-lead arrangement of FIGS. 3-5 to a 2×8 configuration IPG. The extensions may be used to connect to the 2×8 device at one end and to the three leads at the opposite end. The extensions may join at some point between the two ends and transition from 2 sections to three sections.

"Outer" in the context of electrodes forming a tripole set refers to the outer electrodes forming the outer part of a tripole array where the "center" or "medial" electrode(s) form(s) the inner part of the tripole array. In the context of a transverse tripole, the spacing of the outer electrodes from the inner electrode(s) will include a lateral component, where lateral is defined relative to the spinal cord. The outer electrodes may also be referred to as either right or left electrodes. Use of the term, "adjacent" in connection with electrodes refers to electrodes within a configuration or array that are not separated by other electrodes, so "adjacent" electrodes may still be spaced apart or separated from one another.

In the three lead kit 50 illustrated in FIGS. 3-5, each of the first, second and third electric stimulation leads (e.g., right (right-outer), left (left-outer) and center leads 52, 56 and 54) have a distal end portion with a generally cylindrical cross section and at least one stimulation electrode having an exposed, tissue-stimulating portion extending over only a portion of the circumference of the distal end portion (e.g., less than half or less than about 270 degrees for the center electrode). The three lead kit 50 is illustrated as forming a 5-6-5 electrode array in which the outer leads include five electrodes and the center lead include six electrodes, although other electrode arrays are also contemplated including without limitation 4-8-4 electrode arrays.

An exemplary method using this kit 50 generally comprises (a) implanting the first, second and third electric stimulation leads in the epidural space of a patient with (1) the first, second and third electric stimulation leads forming a lead array 50 in the epidural space in which the third electric stimulation lead 54 is disposed between the first and second electric stimulation leads 52 and 56, and (2) the exposed, tissue-stimulating portions of the electrodes 68, 70 and 72 of each electric stimulation lead being oriented at determined angular orientations relative to the spinal cord 66; and (b) programming the stimulation electrodes 68, 70, 72 to create a tripole in which at least one electrode is active on each of the first, second and third electric stimulation leads 52, 56 and 54.

Programming the electrodes may involve varying voltage or current amplitude of electric pulses overlapping in time on the first and second active stimulation electrodes 52 and 56 independently of one another to steer the electrode field generated by the tripole. In TTS, the electrical field can be steered from side to side by varying the current or voltage between the electrodes. Examples include without limitation varying the current or voltage of the two outer electrodes independently of each other, or independently varying the current or voltage between the center electrode(s) and outer electrodes. Voltages or currents may be in phase (overlapping in time) or out of phase between the right and left side.

Also, for example, the first and second active electrodes 52 and 56 may be programmed as anodes and the third active electrode 54 may be programmed as a cathode.

In the example illustrated in FIGS. 3-5, the first, second and third active electrodes 68, 72 and 70 are aligned generally in a direction transverse relative to the spinal cord. As used herein, "transverse tripole stimulation" or "TTS" refers to any arrangement in which at least three electrodes are arranged with a substantial transverse component relative to the neural tissue being stimulated (e.g., along a line that substantially departs from the longitudinal axis of the spine). Examples include without limitation (a) at least three co-linear, epidural electrodes arranged along one or more lead(s) in a line approximately perpendicular to the spinal cord axis, (b) at least three co-linear, epidural electrodes in a line skewed with respect to (i.e. substantially not parallel with) the longitudinal axis of the spinal cord to provide a substantial transverse component to the electrical field generated by the electrodes, and (c) at least three non co-linear, epidural electrodes that provide a substantial transverse component to the electrical field generated by the electrodes, as well as other arrangements in which at least three electrodes are arranged with a substantial transverse component relative to the neural tissue being stimulated.

Also, as further illustrated in FIG. 5, the third active electrode 70 may be oriented in the direction generally facing the spinal cord 66; and the first and second active electrodes 68 and 72 may be oriented at oblique angles relative to the third directional stimulation electrode 70. This may be done for example to protect against shorting out the active electrodes against one another and further to direct the electrical field toward desired targeted tissue of the spinal cord.

In the exemplary two-lead arrangement illustrated in FIGS. 6-8, the segmented or directional electrodes may be manufactured as discussed with respect to the three-lead arrangement illustrated in FIGS. 3-5. In the two-lead arrangement, however, the leads each have an array of inner electrodes and an array or outside electrodes.

FIGS. 6-8 illustrate a two lead kit 100 that may be used in a method of electrically stimulating the spinal cord 66 with first and second electric stimulation leads 102 and 104. Each of the first and second electric stimulation leads 102 and 104 have a distal end portion with a generally cylindrical cross section. The first electric stimulation lead 102 has a first stimulation electrode 106 on the distal end portion thereof with an exposed, tissue-stimulating portion extending over less than half the circumference of the distal end portion. The second electric stimulation lead 104 has second and third stimulation electrodes 108 and 110 on the distal end portion thereof with each of the second and third stimulation electrodes 108 and 110 having an exposed, tissue-stimulating portion extending over less than half of the circumference of the distal end portion.

A method of using the lead kit 100 generally comprises (a) implanting the first and second electric stimulation leads 102 and 104 in the epidural space of a patient with (1) the first and second electric stimulation leads 102 and 104 forming a lead array in the epidural space, and (2) the exposed, tissue-stimulating portions of the first, second and third stimulation electrodes 106, 108 and 110 being oriented at determined angular orientations relative to the spinal cord 66; and (b) programming the stimulation electrodes 106, 108, 110 to create a tripole in which the first, second and third stimulation electrodes 106, 108, 110 are active.

Preferably, the first electric stimulation lead 102 of this example further includes a fourth stimulation electrode 112 on the distal end portion thereof with an exposed, tissue-stimulating portion extending over less than half the circumference of the distal end portion. In this preferred example, the step (a) of implanting the first and second electric stimulation leads 102 and 104 in the epidural space of a patient further includes orienting the first and second electric stimulation leads 102 and 104 such that (i) the third and fourth stimulation electrodes 110 and 112 are disposed at an oblique angle to one another in the direction generally facing the spinal cord 66; (ii) the first stimulation electrode 106 is disposed in a direction generally facing away from the second stimulation lead 104; and (iii) the second stimulation electrode 108 is disposed in a direction generally facing away from the first stimulation lead 102. Most preferably in this example, the first and second electric stimulation leads 102 and 104 are oriented such that: the first stimulation electrode 106 is disposed at an oblique angle generally facing away from the second stimulation lead 104; and the second stimulation electrode 108 is disposed at an oblique angle generally facing away from the first stimulation lead 102.

In this example, the third and fourth stimulation electrodes 110 and 112 may be connected in parallel electrical communication as a common split return path, the first and second stimulation electrodes 106 and 108 may be programmed as anodes, and the voltage of the first and second stimulation electrode may be independently controlled and varied.

Further in the example illustrated in FIGS. 6-8, the third and fourth stimulation electrodes 110 and 112 may be aligned longitudinally within the epidural space relative to one another with the first and second stimulation electrodes 106 and 108 offset longitudinally relative to the third and fourth stimulation electrodes 110 and 112.

In at least one exemplary embodiment of the two-lead arrangement, an active pair of inner electrodes, one on each of the two leads, may be connected in parallel, so that they may be set at a common voltage or effectively form a common split return path, and each outside electrode may be programmed is independently, resulting in 16 total electrodes. For example, the IPG may include one or more switches or other suitable means for selectively connecting one or more of the inner electrodes in parallel. As an exemplary alternative, the IPG or a lead extension may be hardwired to connect the inner electrodes in parallel.

Special extensions may be used to connect the two-lead arrangement illustrated in FIGS. 6-8 to a 2×8 IPG. Each lead connection may have 11 connections, with 6 common to the two leads. The connector rings on the lead may alternatively have a segmented design with a keying feature, so there would be only 6 connector rings, with 5 having two segments per ring. It will be appreciated that other numbers of electrodes may be employed, the illustrated examples merely corresponding to a preferred exemplary embodiment for use with 2×8 IPGs.

U.S. patent application Ser. No. 11/256,220, filed Oct. 21, 2005, by James M. Olsen and Gary W. King, on Transverse Tripole Methods and Systems, published as U.S. Patent Publication No. 2006/0122678, and U.S. provisional application No. 60/621,007, filed Oct. 21, 2004, are hereby incorporated herein by reference. The lead arrangements discussed in this document may be used to form the types of stimulation patterns discussed in U.S. patent application Ser. No. 11/256,220.

Thus, embodiments of the implantable medical electrical leads, kits, systems and methods of use thereof are disclosed. One skilled in the art will appreciate that the present invention can be practiced with embodiments other than those disclosed. The disclosed embodiments are presented for purposes of illustration and not limitation.

What is claimed is:

1. A method of electrically stimulating the spinal cord with a plurality of directional stimulation electrodes on a plurality of electric stimulation leads, each of the electric stimulation leads having a distal end portion with a generally circular cross section on which one or more of the directional stimulation electrode(s) of the plurality are disposed, wherein said plurality of directional stimulation electrodes form an electrode array including at least first, second and third directional stimulation electrodes respectively disposed on first, second and third electric stimulation leads of the plurality of electric stimulation leads, and wherein each directional stimulation electrode of the plurality extends only around a portion of the circumference of the generally circular cross section of the distal end portion on which the directional stimulation electrode is disposed, the method comprising:
   (a) implanting the plurality of electric stimulation leads in the epidural space of a patient with:
      (1) the plurality of electric stimulation leads forming a lead array in the epidural space in which the third electric stimulation lead is disposed between the first and second electric stimulation leads, and
      (2) the first, second and third directional stimulation electrodes being oriented at determined angular orientations relative to the spinal cord such that the third directional stimulation electrode generally faces the spinal cord while the first and the second directional stimulation electrodes are orientated at oblique angles relative to the third directional stimulation electrode; and
   (b) programming the directional stimulation electrodes to create a tripole in which the first, second and third directional stimulation electrodes are active.

2. The method of claim 1 in which the step (b) of programming the directional stimulation electrodes to create a tripole in which the first, second and third directional stimulation electrodes are active includes:
   independently varying the voltage or current amplitude of electric pulses overlapping in time on the first and second directional stimulation electrodes.

3. The method of claim 2 in which the step (b) of programming the directional stimulation electrodes to create a tripole in which the first, second and third directional stimulation electrodes are active further includes:
   programming the first and second directional stimulation electrodes as anodes and the third directional stimulation electrode is programmed as a cathode.

4. The method of claim 1 in which the step (a) of implanting the plurality of electric stimulation leads in the epidural space of a patient further includes:
   aligning the first, second and third directional stimulation electrodes generally in a direction transverse relative to the spinal cord.

5. The method of claim 1 wherein the first and second directional stimulation electrodes each only extends around less than half of the circumference of the distal ends of the first and second electric stimulation leads respectively, and the third directional stimulation electrode extends more than half of the circumference of the distal end of the third electric stimulation lead.

6. A method of electrically stimulating the spinal cord with first, second and third electric stimulation leads, each of the first, second and third electric stimulation leads having a distal end portion with a generally circular cross section and at least one directional stimulation electrode extending only around a portion of the circumference of the generally circular cross section of the distal end portion, the method comprising:
   (a) implanting the first, second and third electric stimulation leads in the epidural space of a patient with:
      (1) the first, second and third electric stimulation leads forming a lead array in the epidural space in which the third electric stimulation lead is disposed between the first and second electric stimulation leads, and
      (2) the directional stimulation electrodes of each electric stimulation lead being oriented at determined angular orientations relative to the spinal cord such that the at least one directional stimulation electrode of the third electric stimulation lead is orientated to generally face the spinal cord and the directional stimulation electrodes of the first and second electric stimulation leads are orientated at oblique angles relative to the at least one directional stimulation electrode of the third electric stimulation lead; and
   (b) programming the directional stimulation electrodes to create a tripole in which at least one electrode is active on each of the first, second and third electric stimulation leads wherein the directional stimulation electrodes programmed as active constitute a first active electrode on the first electric stimulation lead, a second active electrode on the second electric stimulation lead and a third active electrode on the third electric stimulation lead.

7. The method of claim 6 in which the step (b) of programming the directional stimulation electrodes to create a tripole in which at least one electrode is active on each of the first, second and third electric stimulation leads includes:
   varying voltage or current amplitude of electric pulses overlapping in time on the first and second active stimulation electrodes independently of one another.

8. The method of claim 7 in which the step (b) of programming the directional stimulation electrodes to create a tripole in which at least one electrode is active on each of the first, second and third electric stimulation leads further includes:
   programming the first and second active electrodes as anodes and the third active electrode is programmed as a cathode.

9. The method of claim 6 in which the step (a) of implanting the first, second and third electric stimulation leads in the epidural space of a patient further includes:
   aligning the first, second and third active electrodes generally in a direction transverse relative to the spinal cord.

10. The method of claim 6 in which each of the directional stimulation electrodes of the first, second and third electric stimulation leads constitutes a ring electrodes which is shielded to provide electrical insulation and an exposed tissue-stimulation portion of the electrode extending around the portion of the circumference of the generally circular cross section of the distal end portion is exposed through a window that remains unshielded.

11. The method of claim 6 in which each of the directional stimulation electrodes of the first, second and third electric stimulation leads constitutes an arcuate member extending less than half of the circumference of the distal end portion of the first, second or third electric stimulation lead, respectively.

12. A method of electrically stimulating the spinal cord with first, second and third electric stimulation leads, each of the first, second and third electric stimulation leads having a distal end portion with a generally circular cross section on which one or more stimulation electrode(s) are disposed including first and second directional stimulation electrodes on the first and second electric stimulation leads, respectively, and a third direction stimulation electrode on the third electric stimulation lead, wherein each directional stimulation electrode is exposed for tissue stimulation only around a portion of the circumference of the circular cross section of the distal end portion on which the electrode is disposed, and wherein each of the first and second directional stimulation electrodes extends only less than half of the circumference of the circular cross section of the distal end portion on which the electrode is disposed, the method comprising:

(a) implanting the plurality of electric stimulation leads in the epidural space of a patient at determined angular orientations relative to the spinal cord with:
  (1) the plurality of electric stimulation leads forming a lead array in the epidural space with the third stimulation lead disposed between the first and second stimulation lead, wherein the third directional stimulation electrode of the third stimulation lead is orientated to face the spinal cord, and
  (2) the first and second directional stimulation electrodes being oriented at determined angular orientations relative to the spinal cord such that the first and second directional stimulation electrodes are orientated at oblique angles relative to the orientation of the third stimulation lead; and
(b) programming the stimulation electrodes to create a tripole in which the first, second and third stimulation electrodes are active.

* * * * *